United States Patent [19]

Bombardelli

[11] Patent Number: 4,895,839

[45] Date of Patent: Jan. 23, 1990

[54] PHARMACEUTICAL AND COSMETIC COMPOSITIONS CONTAINING COMPLEXES OF FLAVANOLIGNANS WITH PHOSPHOLIPIDS

[75] Inventor: Ezio Bombardelli, Milan, Italy

[73] Assignee: INDENZA S.p.A., Milan, Italy

[21] Appl. No.: 216,039

[22] Filed: Jul. 7, 1988

[30] Foreign Application Priority Data

Jul. 10, 1987 [IT] Italy .............................. 21253 A/87

[51] Int. Cl.$^4$ .................. A61K 31/335; A61K 31/685
[52] U.S. Cl. ....................................... 514/78; 514/452
[58] Field of Search .................................. 514/78, 452

[56] References Cited

U.S. PATENT DOCUMENTS

| | | | |
|---|---|---|---|
| 4,708,964 | 11/1987 | Allen | 514/469 |
| 4,749,573 | 6/1988 | Bonne et al. | 424/195.1 |
| 4,764,508 | 8/1988 | Gabetta et al. | 514/78 |

Primary Examiner—Stanley J. Friedman
Attorney, Agent, or Firm—Bucknam and Archer

[57] ABSTRACT

Topical pharmaceutical or cosmetic compositions having eutrophic and cutis protecting activities, based on complexes of silybin, silydianin, silychristin or mixtures thereof with vegetal or synthetic phospholipids.

1 Claim, No Drawings

PHARMACEUTICAL AND COSMETIC COMPOSITIONS CONTAINING COMPLEXES OF FLAVANOLIGNANS WITH PHOSPHOLIPIDS

The present invention relates to topical pharmaceutical or cosmetic compositions, containing complexes of flavanolignans with phospholipids.

Flavanolignans extracted from a thistle, *Silybum marianum*, namely silybin, silydianin and silychristin as well as the admixture thereof in precise ratios, which admixture is known as silymarin, and also certain extracts, are used in human therapy because of the hepatoprotecting and detoxicant activity thereof, which is at least partly connected to a stabilizing and protecting action for the hepatocyte membrane.

E.P.A. 0209038 discloses phospholipidic complexes of said flavanolignans which, in comparison with the free, uncomplexed form, show advantages as regard bioavalaibility after oral administration.

Now, it has been surprisingly found that the same complexes, or those obtainable from *Silybum marianum* extracts, may be advantageously used in topical pharmaceutical or cosmetic compositions, useful to counteract degenerative and aging phenomena of cutis: said activity, which of course cannot be related to the one traditionally known in hepatology, may find useful applications in the dermatologic field, for example to promote healing process, in the treatment of erythemae, burns, dystrophic conditions of cutis or mucosae, dermatitis, etc. or in the cosmetic field to counteract cutis aging and to protect cutis from atmospheric and environmental agents (rays, wind, sun, etc.).

The activities disclosed in the present invention, particularly the inhibiting activity of aging injuries, seem to be at least partly related to the ability of phospholipidic complexes of flavanolignans to act as free radical scavengers.

In fact, it is already known the remarkable role played by free radicals, which derive from certain cellular metabolisms or from damaging agents such as radiations, etc. in processes related to aging, due to injuring effects on cellular structures of various tissues.

Anyway, the validity of the invention is not connected to the verification of the above assumed mechanism of action.

In the compositions according to the invention, complexes of silymarin or of one or more of its components with natural soy lecithins, such as those defined under the commercial names Lipoid S 30 ro Epicuron 100, consisting of mixtures of phosphatidylcholine, phosphatidylserine and phosphatidylethanolamine, wherein the acyl residues derive mainly from palmitic, stearic, oleic and linoleic acids are preferably used.

The use of natural phospholipids (from soy or animal tissues) is particularly preferred for cosmetic applications, while for more specifically pharmaceutical formulations the use of a chemically homogeneous and defined phospholipid, e.g. distearoyl phosphatidylcholine, may be more appropriate.

The preparation of complexes, which is described in EP 0209038, is carried out by reacting 0.3-2 mole, preferably about 1 mole, of the phospholipid with 1 mole of silybin, silydianin or silychristin, alone or in natural admixture (silymarin), in aprotic organic solvents, such as dioxane, acetone, etc. from which solvents the complex may be recovered by precipitation with non-solvents, such as aliphatic hydrocarbons, or by lyophilization or by nebulization.

Preparation of the formulations according to the invention is carried out by means of conventional techniques and excipients, as described in "Remington's Pharmaceutical Sciences Handbook", Hack Pub. Co., N.Y. U.S.A.

Phospholipid complexes of flavanolignans may be used also in form of microdispersions in water, which are obtained by homogenization by means of high-speed or ultra-sonic stirrers, said microdispersions being optionally added with thickening or suspending agents.

Examples of suited formulations comprise creams, gels, ointments, lotions or other formulations conventionally used for topical administration. It is also possible to envisage plasters, gauzes, pads or garments imbued with the above mentioned active principles.

Other known active ingredients, having complementary or anyway useful activities for the intended therapeutic and/or cosmetic uses, may be present besides the phospholipid complexes of flavanolignans.

For example, the compositions of the invention may optionally contain vitamins, amino acids, vegetal extracts, emollients, antibacterial agents, topical antiinflammatory agents, etc.

Phospholipid complexes of silymarin or of the components thereof will be present in the formulations of the invention at percentages from 1 to 10 by weight. The administration procedures will obviously depend on the particular selected form and on the type of administration: generally, it will be sufficient to cover the cutis area to be treated with a thin layer of cream, gel or lotion 1 to 3 times a day, for times even longer than some months.

The following non-limiting examples further illustrate the invention.

PREPARATION 1

Sylimarin-soy phosphatidylcholine 1:1 complex

A solution of 5 g of silymarin in 100 ml of acetone was treated with 8 g of "Lipoid S 100 ®", under stirring at room temperature. After complete solubilization, the raction mixture was concentrated under vacuum to 30 ml and poured into 300 ml of ligroin, under stirring. The precipitate was left to settle overnight, then it was collected by filtration, washed with ligroin and dried under vacuum at 40° C. 11.2 g of the complex were obtained.

$E_{1\%} = 170.2$ at 288 nm ($CH_3OH$).

PREPARATION 2

Silybin-soy phosphatidylcholine 1:2 complex

A suspension of 4.82 g of silybin (0.010 mole) in 75 ml of dioxane was treated under stirring with a suspension containing 15.4 g (0.020 mole) of "Lipoid S 100 ®". After 4 hours the reaction mixture became clear and it was lyophilized. 20 g of the complex of light yellow colour, was obtained.

$E_{1\%} = 106$ at 288 nm ($CH_3OH$).

E1. Analysis (MW=2022); calc. % N=1.38; P=3.07; found % N=1.35; P=3.11.

PREPARATION 3

Silybin-soy phosphatidylcholine 1:0.3 complex

A solution of 2.41 g (0.005 mole) of silybin in 100 ml of dioxane was treated at 60° C. with 0.770 g (0.001 mole) of "Lipoid S 100 ®" for 1 hour. The reaction mixture was evaporated to dryness under vacuum and the residue was taken up into 100 ml of chloroform.

Uncomplexed silybin, present as sediment, was removed by filtration and mother liquors containing the complex were evaporated to dryness under vacuum.

The obtained residue, dried at 30° C. under vacuum, consisted of 2.3 g of the complex, in form of a white yellowish powder.

$E_{1\%} = 300$ at 288 nm (CH$_3$OH).

PREPARATION 4

A solution of 10 g of silymarin in 150 ml of acetone was treated with 20 g of "Lipoid S 100 ®" under stirring at room temperature.

After complete dissolution, the reaction mixture was concentrated to small volume under vacuum.

The viscous residue was dried under vacuum at 45° C. during a night. 29 g of the product was obtained, which was yellow-beige in colour and spectroscopically agreed with complex from EP 0209038.

PREPARATION 5

Silymarin-distearoylphosphatidylcholine 1:1 complex

A solution of 10 g of silymarin in 150 ml of acetone was treated with 10 g of distearoylphosphatidylcholine under stirring at room temperature. The reaction mixture was evaporated to small volume under vacuum. The viscous residue was washed with ligroin and dried under vacuum at 40° C.; 18.8 g of a product, whose spectroscopical data were in agreement with a complex structure, were obtained.

The activities of the compositions according to the invention are illustrated as an example, by the comparison of the effect on croton oil oedema of silymarin, silymarin-distearolyphosphatidylcholine complex (according to preparation 5), distearoylphostphatidylcholine and indomethacine.

The data reported in the table which follows show that local application of silymarin and to a greater extent of the silymarin-distearoylphosphatidylcholine complex cause a dose-dependent anti-oedema action, well comparable with the indomethacine's one.

On the contrary, distearoylphosphatidylcholine starts a modest activity, largely inferior to the one of the silymarin-distearoylphosphatidylcholine.

TEST FROM CROTON OIL (Tubaro et al., Agents Actions 17, 347, 1985)

Animals

Male mice of albino race, Swiss stock CD 1 Charles River.

Method

Application of croton oil and of the substance under exam, in ethyl acetate solution, on the internal surface of the mouse's right ear. At the end of the experiment, that is 6 h after application of croton oil and of the substance under exam, the animals were sacrificed. Evaluation of the oedema answer was carried out by measuring the difference in weight between a well defined area taken from the treated ear and an analogous one taken from the untreated ear.

| SUBSTANCES | No. ANIMALS | DOSE/EAR mcg | OEDEMA ± ES mg | % REDUCTION | P< (ANOVA) |
|---|---|---|---|---|---|
| Controls | 27 | 67.5 | 7.1 ± 0.2 | — | — |
| Silymarin | 14 | 480 | 2.2 ± 0.4 | 69.0 | 0.001 |
|  | 13 | 240 | 3.0 ± 0.4 | 59.5 | 0.001 |
|  | 13 | 120 | 4.5 ± 0.5 | 39.2 | 0.001 |
|  | 14 | 48 | 6.2 ± 0.3 | 12.7 | 0.005 |
| Silymarin/distearoylphosphatidylcholine | 14 | 1270 | 0.5 ± 0.2 | 93.0 | 0.001 |
|  | 14 | 635 | 0.8 ± 0.2 | 89.2 | 0.001 |
|  | 14 | 317 | 3.9 ± 0.5 | 47.3 | 0.001 |
|  | 14 | 127 | 3.7 ± 0.6 | 47.9 | 0.001 |
| Distearoylphosphatidylcholine | 14 | 790 | 5.2 ± 0.5 | 26.8 | 0.001 |
|  | 14 | 395 | 6.5 ± 0.3 | 8.5 | 0.05 |
|  | 13 | 197 | 5.9 ± 0.3 | 16.9 | 0.001 |
|  | 14 | 79 | 6.3 ± 0.3 | 11.3 | 0.01 |
| Indomethacine | 13 | 142 | 4.7 ± 0.6 | 33.8 | 0.001 |

Some examples of formulations according to the invention are reported hereinbelow.

EXAMPLE 1

Cream Containing a Silymarin-soy Phosphatidylcholine Complex as the Active Ingredient

| Formulation for 100 g of cream | |
|---|---|
| Complex of preparation 1 | 2.0 g |
| Polyethyleneglycol | 2 g |
| Polysorbate 80 | 3 g |
| Cetyl alcohol | 10 g |
| Wheat germ oil | 2 g |
| Silicon oil 350 cps | 0.5 g |
| Antioxidants (oxinex ® 2004) | 0.1 g |
| Carboxyvinylpolymer (Carbomer 934 ®) | 0.8 g |
| Triethanolamine | 1.2 g |
| Preservants (a mixture of methyl and propyl p-hydroxybenzoates) | 0.2 g |
| Perfumed composition | 0.1 g |
| Depurated water q.s. to | 100 g |

EXAMPLE 2

Gel containing a Silybin-soy Phosphatidylcholine Complex as the Active Ingredient

| Formulation for 100 g of gel | |
|---|---|
| Complex of preparation 2 | 1 g |
| Imidazolidinylurea | 0.3 g |
| Octilinone | 0.1 g |
| C$_8$-C$_{12}$ ethoxylated triglycerids (Softigen 767 ®) | 25 g |
| Polyoxyethylene 20 oleylether | 5 g |
| Carboxyvinylpolymer (Carbomer 934 ®) | 1.5 g |
| Triethanolamine | 2 g |
| Perfumed composition | 0.1 g |
| Depurated water | 65 g |

EXAMPLE 3

Lotion Containing a Silymarin-soy Phosphatidylcholine Complex as the Active Ingredient

| Formulation for 100 g of lotion | |
|---|---|
| Complex of preparation 4 | 1 g |
| Imidazolidinylurea | 0.3 g |
| Octilinone | 0.1 g |
| PEG-6-caprylic/capric glyceride | 25 g |
| Polyoxyethylene 20 oleylether | 5 g |
| Perfumed composition | 0.1 g |
| Water q.s. to | 100 g |

I claim:

1. The method of treating edema in a host in need of such a treatment which consists of topically applying to the edema an effective amount of a composition which contains as the active ingredient 1–10% by weight of a flavannolignan complex, selected from the group consisting of silymarin, silybin, silydianin and silychristin, with a phospholipid, which is a synthetic mixture of phosphatidylcholine, phosphatidylserine and phosphatidylethanolamine, wherein the acyl residues are derived from palmitic, stearic, oleic and linoleic acids or a natural phospholipid in admixture with excipients.

* * * * *

UNITED STATES PATENT AND TRADEMARK OFFICE
CERTIFICATE OF CORRECTION

PATENT NO. : 4,895,839
DATED : JANUARY 23, 1990
INVENTOR(S) : EZIO BOMBARDELLI

It is certified that error appears in the above-identified patent and that said Letters Patent is hereby corrected as shown below:

On the title page

Item (73) ASSIGNEE

THE NAME OF THE ASSIGNEE SHOULD BE:
   INDENA S.P.A.

Signed and Sealed this

Seventeenth Day of December, 1991

Attest:

HARRY F. MANBECK, JR.

Attesting Officer

Commissioner of Patents and Trademarks